(12) United States Patent
Falco

(10) Patent No.: US 10,034,798 B2
(45) Date of Patent: Jul. 31, 2018

(54) HEARING PROTECTOR WITH CURVED SEGMENTS

(71) Applicant: 3M INNOVATIVE PROPERTIES COMPANY, St. Paul, MN (US)

(72) Inventor: Robert N. Falco, Indianapolis, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 599 days.

(21) Appl. No.: 13/795,790

(22) Filed: Mar. 12, 2013

(65) Prior Publication Data

US 2013/0186415 A1 Jul. 25, 2013

Related U.S. Application Data

(63) Continuation of application No. 11/270,053, filed on Nov. 9, 2005, now Pat. No. 8,596,279.

(51) Int. Cl.
*A61F 11/08* (2006.01)
*A61F 11/12* (2006.01)

(52) U.S. Cl.
CPC .............. *A61F 11/08* (2013.01); *A61F 11/12* (2013.01)

(58) Field of Classification Search
CPC ................................................ A61F 2011/085
USPC ......... 128/864–868; 181/128–130, 134, 135; 381/380, 71.1, 71.6
See application file for complete search history.

(56) References Cited

U.S. PATENT DOCUMENTS

| | | | |
|---|---|---|---|
| 2,458,884 A | 1/1949 | Volkmann | |
| 2,717,596 A | 9/1955 | Knight | |
| 4,314,553 A | 2/1982 | Westerdal | |
| 5,074,375 A | 12/1991 | Grozil | |
| 5,781,272 A * | 7/1998 | Bright et al. | 351/123 |
| 5,809,574 A * | 9/1998 | Falco et al. | 2/209 |
| 6,176,576 B1 * | 1/2001 | Green et al. | 351/123 |
| 6,241,041 B1 | 6/2001 | Leigh | |
| 7,314,047 B2 | 1/2008 | Falco | |
| 7,727,433 B2 | 6/2010 | Knauer | |
| 7,731,487 B2 | 6/2010 | Knauer | |
| 7,743,771 B2 | 6/2010 | Falco | |
| 2004/0045558 A1 | 3/2004 | Taylor | |
| 2004/0129276 A1 | 7/2004 | Kuno | |
| 2006/0162992 A1 | 7/2006 | Seville | |
| 2007/0102006 A1 | 5/2007 | Falco | |

FOREIGN PATENT DOCUMENTS

| | | |
|---|---|---|
| CN | 2674810 | 1/2005 |
| WO | 98/06363 | 2/1998 |
| WO | 99/44556 | 9/1999 |
| WO | 02/43633 | 6/2002 |
| WO | 2004/036953 | 4/2004 |
| WO | WO 2005/122981 | 12/2005 |
| WO | 2006/078767 | 7/2006 |

OTHER PUBLICATIONS

European Application No. 13180132 Extended Search Report dated Sep. 13, 2013.

* cited by examiner

*Primary Examiner* — Tarla Patel
(74) *Attorney, Agent, or Firm* — Christopher D. Karlen (57) ABSTRACT

A hearing protection device is provided including a sound attenuating element and a stem extending from the sound attenuating element, wherein the stem comprises multiple curved segments.

19 Claims, 9 Drawing Sheets

HEARING PROTECTOR WITH CURVED SEGMENTS

TECHNICAL FIELD OF INVENTION

The invention concerns hearing protection devices and, more particularly, a hearing protector including a sound attenuating element and a stem extending from the sound attenuating element, the stem including multiple curved segments.

BACKGROUND OF INVENTION

The use of hearing protective and noise attenuating devices is well known, and various types of devices are available including, but not limited to, ear muffs, semi-aural devices, and earplugs. Earplugs are often preferred for their effectiveness in attenuating sound and for comfort properties provided thereby.

An earplug generally comprises a sound attenuating element which is placed in the ear canal of a wearer to occlude the canal and thus provide a desired sound attenuation. The sound attenuating element is commonly made of a compressible, resilient material such as a foam or a rubber.

The earplug may further include a stem embedded partly or entirely in the resilient sound attenuating element. The stem provides a degree of rigidity to the earplug which enables the earplug to be easily inserted and pushed into the ear canal of a user. Further, where the stem extends from the sound attenuating element, it may serve as a handle of the earplug to facilitate insertion and removal of the earplug.

Commonly, the stem is a cylindrical member which extends from the sound attenuating element along a longitudinal axis of the earplug. That is, the stem extends in a straight line rearwardly from the sound attenuating element in a collinear manner with respect to the attenuating element. Thus, the stem is available as a handle when inserting and removing the earplug. When the earplug is inserted into the ear canal, the stem extends outwardly from the ear and may be grasped and adjusted by the wearer as desired.

However, in this configuration, the stem is left exposed to inadvertent contact. For example, the user may accidentally strike the stem with their hands while adjusting their hair, attending to an itch, when adjusting clothes, etc. Further, the wearer may inadvertently contact the exposed stem while applying or adjusting headwear such as a hat, or additional safety protection equipment such as protective eyewear, a helmet, a respirator, etc. Still further, the exposed stem may be inadvertently contacted by another person or an outside object such as machinery, building structures, etc.

This type of incidental contact may slightly dislodge the stem, thus reducing the attenuation provided by the earplug. This slight dislodgement may even go unnoticed by the wearer, thus subjecting the wearer to reduced levels of attenuation over extended time periods. Such inadvertent contact may be sufficient to entirely expel the earplug from the ear canal all together, therefore exposing the wearer to all external noise until the earplug is properly re-inserted. Further, certain incidental contacts may force the stem inward toward the inner ear or may pivot the stem within the ear canal, thus causing discomfort to the wearer.

Often, these conventionally stemmed earplugs are provided in corded pairs. Each pair includes a cord extending between the stems of the respective earplugs. The cord is typically attached to the exposed rear end of the stem and extends from the earplug, at least initially, in a collinear manner with respect to the stem and the sound attenuating element. When a corded pair of earplugs is worn, the cord (like the stem) extends outwardly from the ear and generally outwardly from the head of the wearer. More specifically, the cord initially extends outwardly for a length, in line with the stem, and then curves downward and eventually drapes beneath the chin or behind the neck of the wearer. This extension of the cord essentially increases the contactable portion of the inserted earplug. When such earplug is worn, the exposed stem is vulnerable to inadvertent contact as well as the projecting portion of the cord. That is, the projecting portion of the cord may suffer unintentional tugging or tangling which could result in partial or complete dislodgement of the earplug from the ear canal.

Thus, a stem for an earplug is desired which is sufficient for handling, inserting, and removing the earplug and which is positioned and configured to reduce the incidence of inadvertent contact, even when corded.

BRIEF SUMMARY OF THE INVENTION

The above discussed and other problems and deficiencies of the prior art are overcome or alleviated by the invention which provides a novel and nonobvious hearing protection device.

The invention provides a hearing protector including a sound attenuating element and a stem extending from the sound attenuating element. In an exemplary embodiment, the stem includes multiple curved segments.

The above-discussed and other features and advantages of the apparatus and method of the invention will be appreciated and understood by those skilled in the art from the following drawings and detailed description.

BRIEF DESCRIPTION OF THE FIGURES

Referring now to the drawings wherein like elements are numbered alike in the several FIGURES.

DETAILED DESCRIPTION OF THE PREFERED EMBODIMENT

FIGS. 1-5 shows a stem 10 for an earplug 50 (see, FIGS. 6-10), in one exemplary embodiment of the invention. The stem 10 generally includes a handle portion 12 and an attachment portion 14 extending therefrom. As will be discussed herein in detail, the handle portion 12 is configured and oriented to facilitate handling ear canal insertion, and ear canal removal of the earplug 20 while remaining adjacent to the outer ear and head of the wearer to thus minimize incidental contact therewith. The attachment portion 14 is configured for receiving and retaining a sound attenuating portion 52 (FIGS. 6-10) of the earplug 50.

The handle portion 12 of the stem 10 includes a proximate portion 16 and an opposing distal portion 18. As shown in FIGS. 1-5, the proximate portion 16 is disposed near the attachment portion 14. The distal portion 18 is adjacent to the proximate portion 16, opposite from the attachment portion 14. The proximate portion 16 extends generally along an axis A-A shared with the attachment portion 14. (See, particularly, FIG. 1.)

Figure 1:
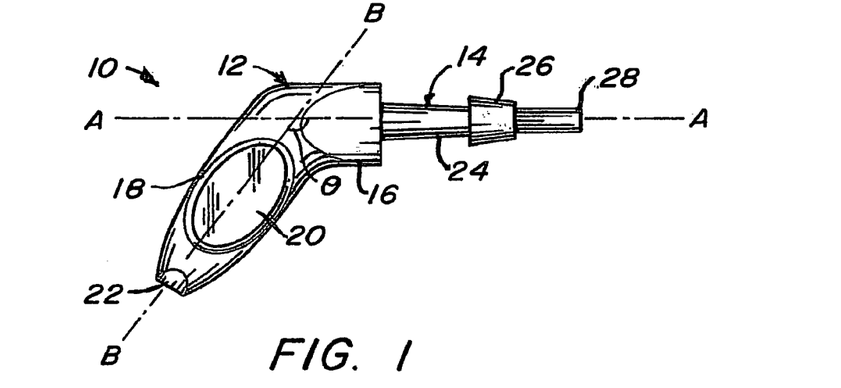
FIG. 1 is a side view of an earplug stem in one embodiment of the invention.
Figure 2:
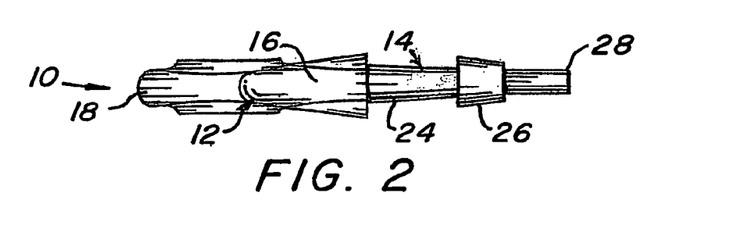
FIG. 2 is a top view thereof.
Figure 3:
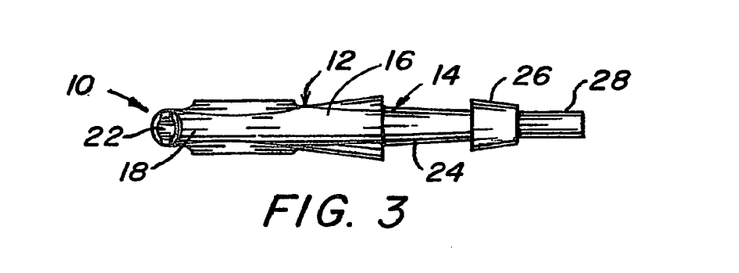
FIG. 3 is a bottom view thereof.
Figure 4:
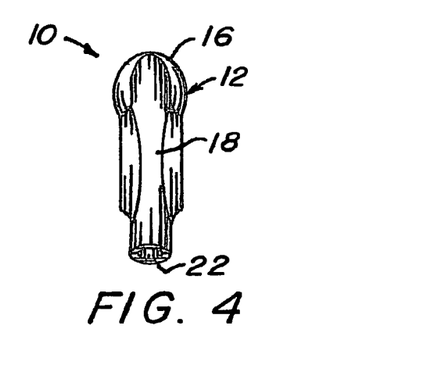
FIG. 4 is a rear view thereof.
Figure 5:
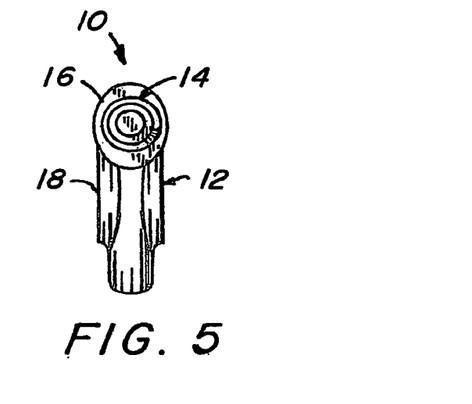
FIG. 5 is a front view thereof.
Figure 6:
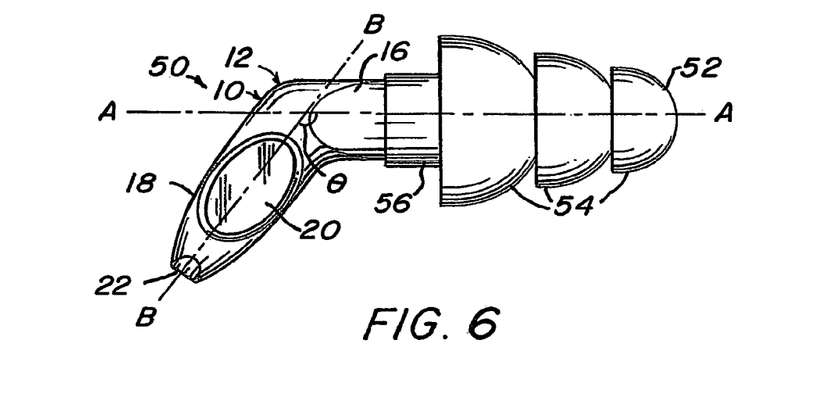
FIG. 6 is a side view of an earplug having the stem of FIGS. 1-5.
Figure 7:
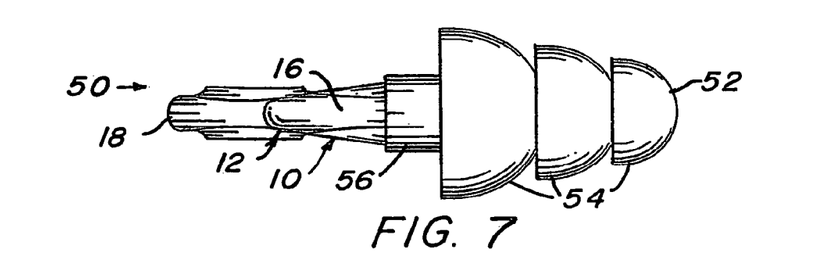
FIG. 7 is a top view thereof.
Figure 8:
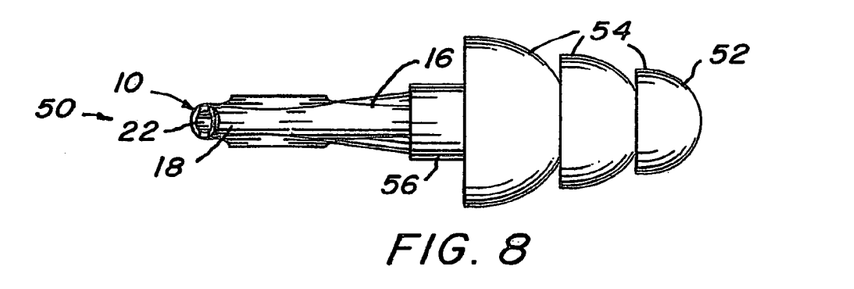
FIG. 8 is a bottom view thereof.
Figure 9:
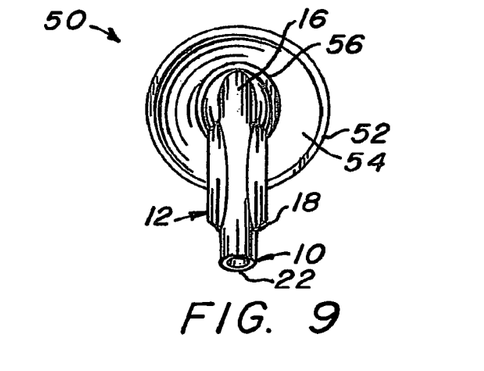
FIG. 9 is a rear view thereof.
Figure 10:
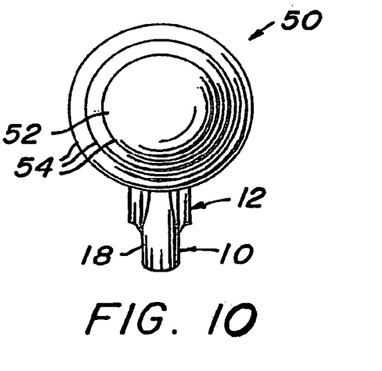
FIG. 10 is a front view thereof.
Figure 11:
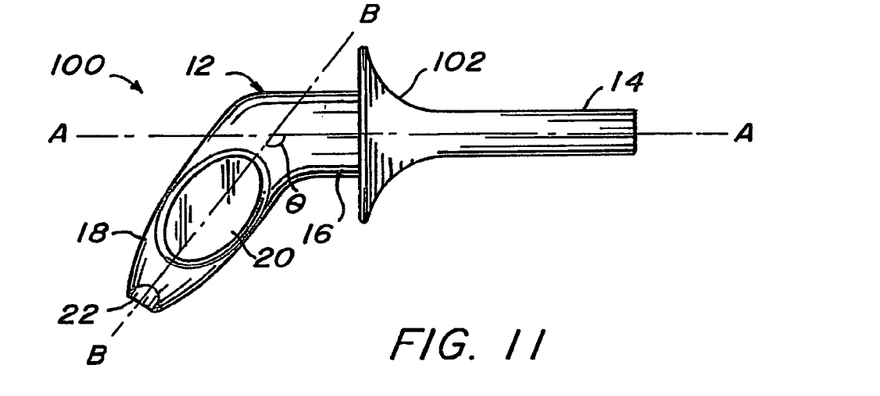
FIG. 11 is a is a side view of an earplug stem in another embodiment of the invention.
Figure 12:
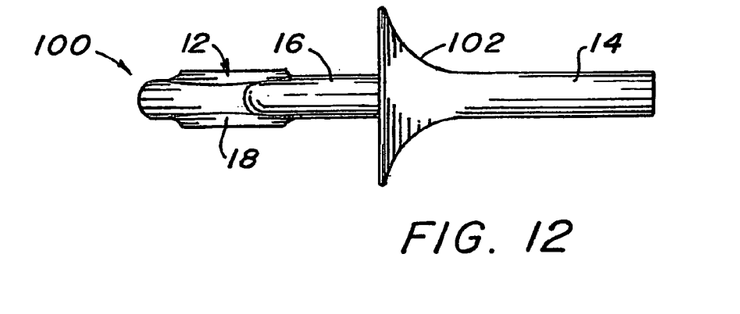
FIG. 12 is a top view thereof.
Figure 13:
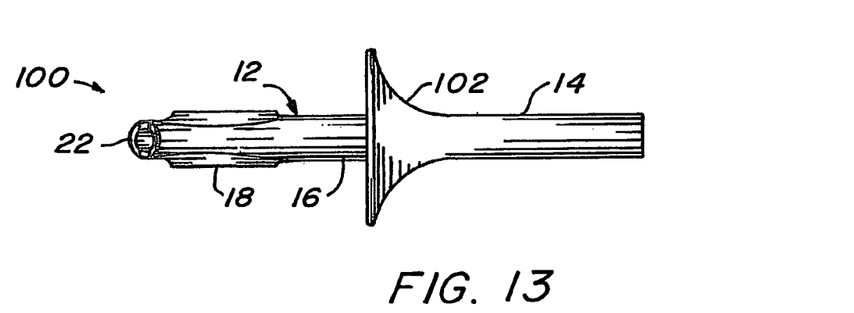
FIG. 13 is a bottom view thereof.
Figure 14:
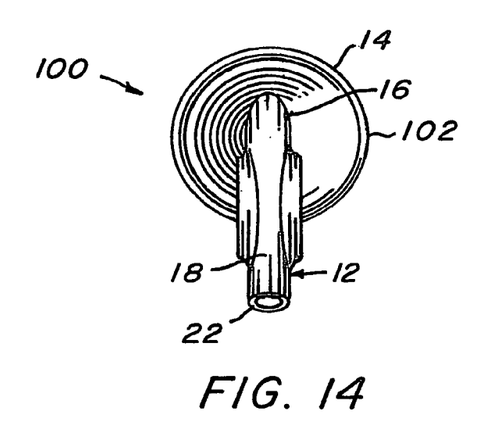
FIG. 14 is a rear view thereof.
Figure 15:
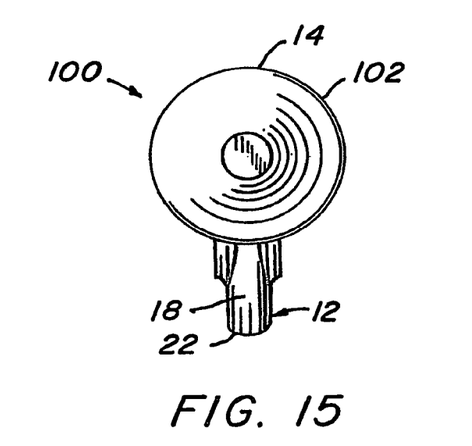
FIG. 15 is a front view thereof.
Figure 16:
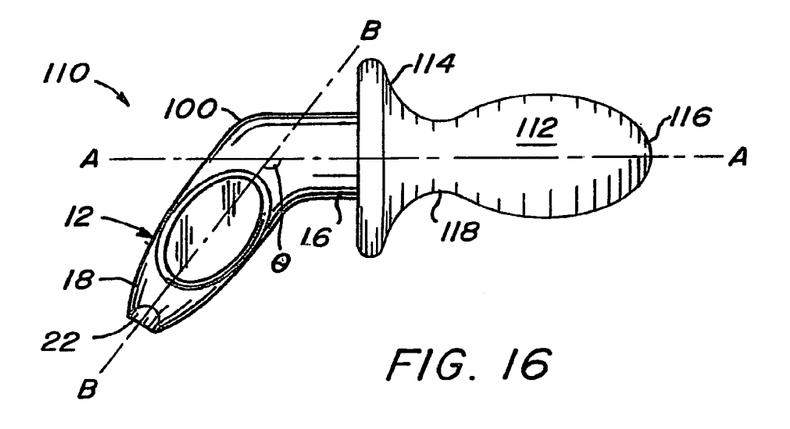
FIG. 16 is a side view an earplug having the stem of FIGS. 11-15.
Figure 17:
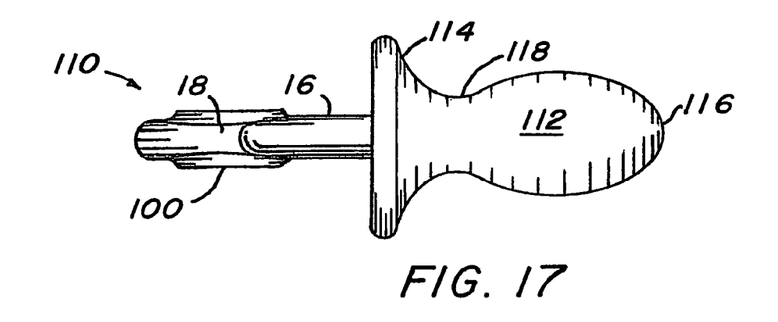
FIG. 17 is a top view thereof.
Figure 18:
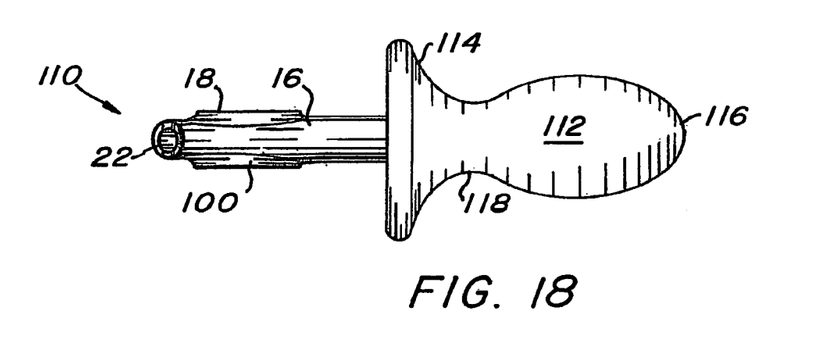
FIG. 18 is a bottom view thereof.
Figure 19:
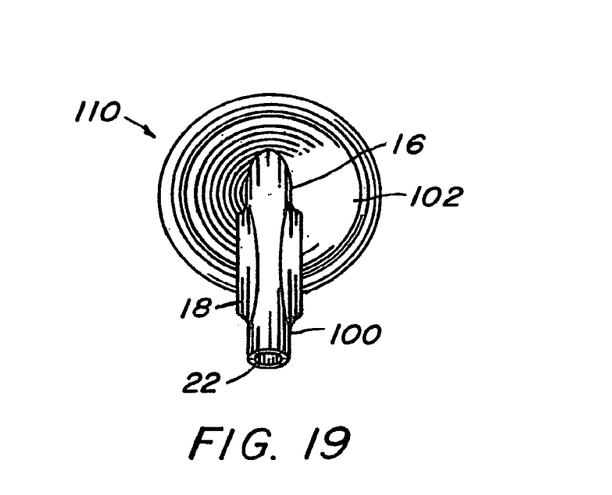
FIG. 19 is rear view thereof.
Figure 20:
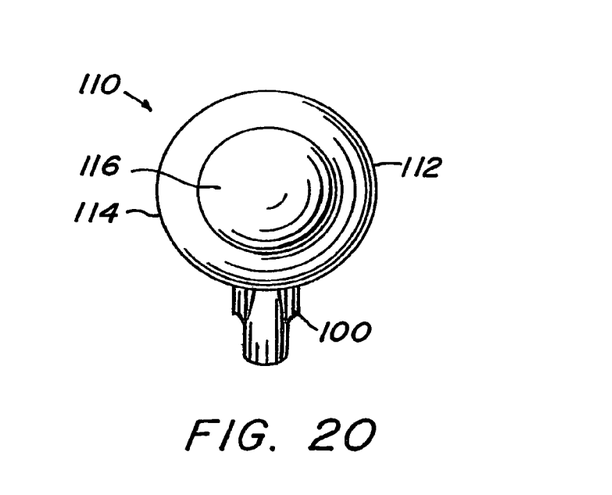
FIG. 20 is a front view thereof.

The distal portion 18 diverges from the proximate portion 16 along an axis B-B. The axis B-B is disposed at an angle Θ relative to the axis A-A. The angle Θ is generally greater than 90° and preferably between 110° and 140°. In the present exemplary embodiment, the angle Θ is generally less than or equal to approximately 125°. In other words the axis B-B is not collinear with the axis A-A. The distal portion 18 includes a handling area 20 disposed approximately midway along a length of the portion 18. The handling area 20 comprises a contoured surface for facilitating retention of the stem 10 between fingertips of the wearer. For example, the handling area 20 may comprise an oval shaped surface having planar and/or curvilinear features. That is, the handling area 20 may be flat, convex, concave, or any combination of these. The area 20 may additionally and/or alternatively include grip features which are disposed inset or in relief relative to the feature 20, such as score lines, protuberances, etc. The handling area 20 may further include indicia, symbols, etc., such as trade names, product names, etc. These may be printed at the handling area 20 or formed thereon in relief or in an inset fashion.

Figure 21:
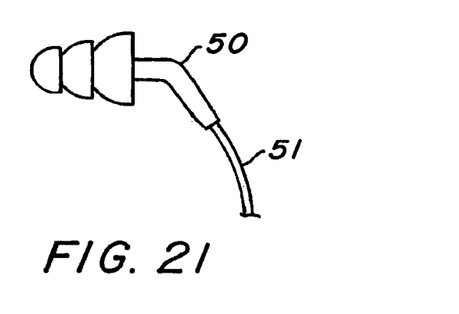
FIG. 21 is a perspective view of an earplug according to FIGS. 6-10 having a cord attached thereto.

The distal portion 18, in an exemplary embodiment includes an aperture 22 formed at an end opposite from the proximate portion 16. The aperture 22 extends along the axis A-A, forming a cavity within the distal portion 18. The aperture 22 and resulting cavity are generally circular in cross-section and are configured to receive and retain a cord 51 as shown in FIG. 21. The cord 51 allows the resulting earplug 50 to be attached to another earplug 50 to form a connected pair of earplugs 50. The cross-section of the aperture 22 may be sized slightly smaller than that of the cord 51 such that the cord is held therein in a friction fit. Additionally and/or alternatively, the cord 51 may be bonded to the distal portion 18 in the aperture by way of an adhesive agent, an in situ molding process, etc.

The attachment portion 14 includes features which facilitate attachment of the sound attenuating element 52 with the stem 10. These features may include, for example, a first conical portion 24 which has a generally serially decreasing circular cross-section and tapers toward a front of the attachment portion 14, and a second conical portion 26 adjacent to the portion 24 where the portion 26 also includes a serially decreasing circular cross-section in a direction toward the front of the attachment portion 14. The portion 14 also includes a front end 28 which is generally a cylindrical member extending away from the second conical portion 26. These features 24, 26, and 28 are specifically shaped, disposed, and configured to aid in affixing the sound attenuating element 52 to the stem 10. Namely, these features 24, 26, 28 include shapes and surfaces which readily receive and retain the material which forms the sound attenuating element 52 and/or any bonding agent which may be used facilitate said affixation.

FIGS. 6-10 show the earplug 50 having the sound attenuating element 52 attached to the stem 10. Here, by way of example, the sound attenuating element 52 is shown as comprising a plurality of rearwardly facing semi-spherical flanges 54. Three such flanges 54 are shown. Of course, the earplug 50 may include more or less of the flanges 54 (e.g., four or more flanges, two flanges, a single flange, etc.) A base 56 of the sound attenuating element is disposed partly on the proximate portion 16 of the stem 10. Here, the sound attenuating element 52 may be formed of a thermoplastic elastomer (TPE), or any suitable compressible material. The sound attenuating element 52, for example, may be similar or identical to that disclosed in U.S. Pat. No. 4,867,149, issued on Sep. 19, 1989, the contents of which are herein incorporated by reference in their entirety. The sound attenuating element 52 may be pre-molded and then affixed to the stem 10 by an adhesive bonding agent. Further, such a pre-molded attenuating element 52 may be affixed on the stem 10 by way of a friction fit. In such embodiment, the attenuating element 52 is formed with a receptacle at its interior configured to receive and retain the attachment portion 14 of the stem 10. The receptacle may have a cross-sectional area smaller than that of the attachment portion 14 of the stem 10 such that the friction fit is establish upon inserting the stem 10 into the receptacle. Additionally, the attachment features 24, 26, 28 of the attachment portion 14 may be configured to mate or create a snap-fit with the interior of the sound attenuating portion 52 at the receptacle. That is, the portion 14 and the receptacle can include interlocking features such as male and female elements, etc. In a further alternative embodiment, the element 52 is simply molded directly onto the stem 10.

Figure 29:
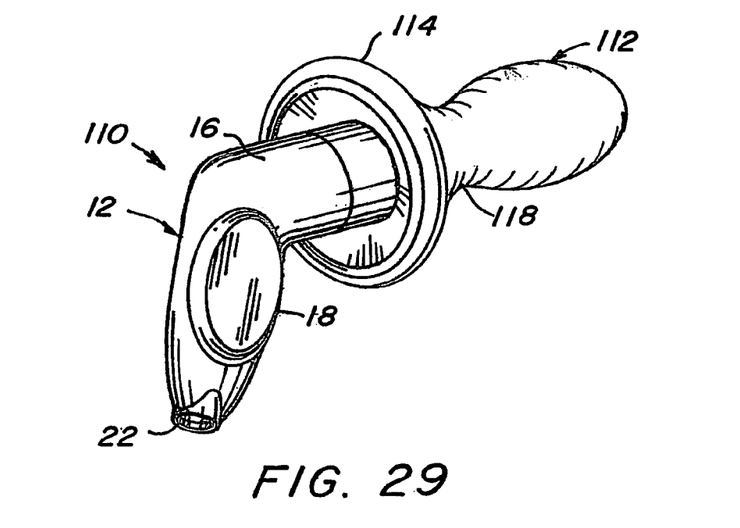
FIG. 29 is a rear perspective view of the earplug of FIGS. 16-20.

FIGS. 12-15 and 28 show a stem 100 in another embodiment of the invention. The stem 100 is similar in many respects to the stem 10 discussed above. Features which are consistent between the various embodiments of the invention discussed herein are indicated by consistent reference numerals and, for sake of brevity, are not reintroduced or discussed in substantive detail. The stem 100 includes the handle portion 12 extending along the axis B-B and the attachment portion 14 extending along the axis A-A, where the axes intersect at the angle 8. The stem 100 further includes a flange 102 disposed on the attachment portion 14 near the proximate portion 16 of the handle portion 12. The flange 102 is generally a rearwardly extending funnel-shaped member which opens toward the handle portion 12 of the stem 100. As shown in the drawings, the flange 102 assumes a generally conical shape. A space is delimited beneath the flange 102, between the flange 102 and a part of the proximate portion 16 of the stem handle portion 12. See particularly, FIGS. 28-29. This space allows the flange 102 to collapse, as necessary, when inserting the earplug 110 into the ear canal to thus provide a secure and complete fit. The attachment portion 14 of the stem 100 further comprises an elongated substantially cylindrical member which extends from the flange 102 toward a front of the stem 100.

FIGS. 16-20 and 29 show an earplug 110 formed of the stem 100 and a sound attenuating element 112. Here, the attenuating element 112 is affixed to the stem 100 over the attachment portion 14 and on to the flange 102. That is, a rear 114 of the sound attenuating element 112 proximate to the handle portion 12 abuts and is attached to the flange 102, as shown in the drawings. A front 116 of the sound attenuating element 112 includes a rounded shape, such as a semi-hemispherical, semi-elliptical, etc. shape, in order to facilitate insertion of the earplug 110 into the ear canal of a wearer. The sound attenuating element 112 further includes a tapered portion 118 disposed between the front 116 and rear 114. The tapered portion 118 is an area of reduced cross-sectional area which extends generally in a middle portion of the sound attenuating element 112. Of course, the element 112 may alternatively include a substantially cylindrical shape of generally uniform cross-sectional diameter. Still further, the sound attenuating element 112 may comprise spherical shape, a rearwardly extending flange shape, or any desired shape and/or configuration. The space beneath the flange 102 is maintained upon attachment of the sound attenuating element 112. See, FIG. 29. As mentioned, this space allows collapse of the flange 102 and the rear 114 of the attenuating portion 112 to facilitate fitting of the earplug 110 within the ear canal.

Figure 22:
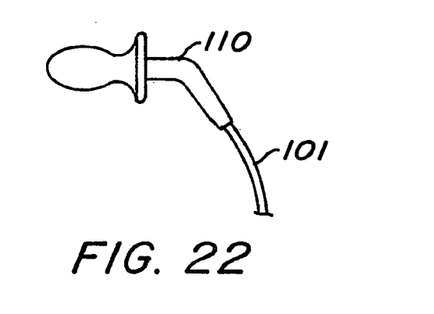
FIG. 22 is a perspective view of an earplug according to FIGS. 16-20 having a cord attached thereto.

Like the earplug 50, the earplug 110 includes the aperture 22 formed in the stem 100 for receipt and retention of a cord 101, as shown in FIG. 22. The cord 101 is configured to be similarly attached to a second earplug 110 to thus form a corded pair of earplugs 110. The cord 101 may be friction fit within the aperture 22 or bonded to or molded therewith.

The sound attenuating element 112 of the earplug 110 is formed preferably of a compressible, resilient slow recovery foam material such as polyvinylchloride (PVC) or polyurethane. For example, the sound attenuating element 112 may be composed of a material as that described in U.S. Pat. No. Re. 29,487 issued on Dec. 6, 1977, the contents of which are herein incorporated by reference in their entirety.

The sound attenuating element 112 may be preformed and then attached to the stem 110 by an adhesive bonding agent. Here, the bonding agent may be applied to the portion of the flange 102 which contacts the rear 114 of the attenuating element 112. Additionally and/or alternatively, the bonding agent may be applied to the front end of the attachment portion 14 and/or along the length thereof. In another embodiment, the element 112 may be formed directly on the stem 100 such that the element 112 is mechanically bonded thereto. For example, where the sound attenuating element 112 is a foam material, the element 112 may be formed in a mold around the attachment portion 14 so as to bond thereto. Here, the flange 102 serves to stop the expanding foam during formation of the element 112. The flange 102 also acts as a bonding surface and facilitates in the shaping of the resulting element 112. In an alternate embodiment, the sound attenuating element 112 may be dip-molded onto the stem 100 according to know techniques. In a further embodiment, the sound attenuating element 112 may be friction fit onto the stem 100. For example, the element 112 may be preformed to include a receptacle at an interior thereof for receiving and retaining the attachment portion 14 of the stem 100. The receptacle may include a cross-sectional area slightly smaller than that of the attachment portion 14 so as to create the friction fit when the portion 14 is inserted into the receptacle. Alternatively and/or additionally, the attachment portion 14 and the interior of the receptacle may be configured to facilitate a mating or a snap-fitting of the sound attenuating element 112 onto the stem 100. For example, the attachment portion 14 and the sound attenuating element 112 may include interlocking (i.e., male and female) features in order to facilitate the friction fit or snap-fit.

The handle portion 12 of the earplugs 50, 110 described herein may be substantially cylindrical in shape, having a generally consistent cross-sectional diameter across its length. Alternatively, the handle portion 12 can include cross-sections of variable diameter such that an area(s) of the handle 12 tapers inwardly and/or outwardly. In another embodiment, the handle portion includes a rectilinear or elliptical cross-section of consistent or variable cross-sectional area. Further, the handle portion 12 may include a combination of some or all of these configurations and/or further configurations as desired.

Figure 23:
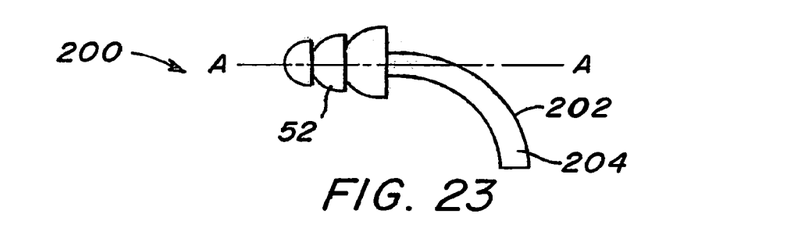
FIGS. 23-25 are side views of earplugs in other embodiments of the invention.
Figure 24:
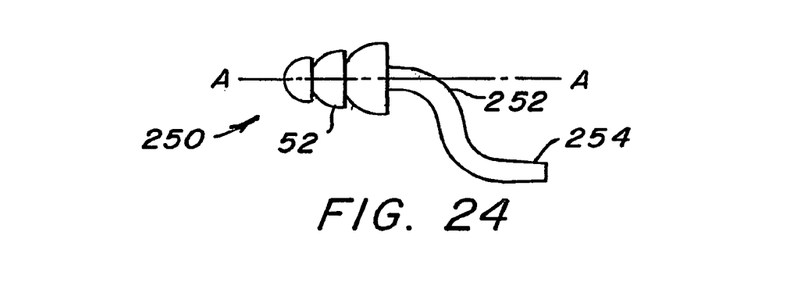

For example, FIG. 23 shows an earplug 200 having the sound attenuating portion 52 attached to a stem 202. The stem 202 includes the attachment portion 14 (not shown) and a curved handle 204. The handle 204 traces a curve as shown such that at least a portion of the handle 204 is offset from and non-collinear with the axis A-A of the sound attenuating element 52. The curve of the handle 204 may be a portion of a radius of a circle, a portion of an ellipse, or any other desired curve. FIG. 24 shows an earplug 250 in another embodiment of the invention. The earplug 250 includes a stem 252 which includes the attachment portion 14 (not shown) affixed to the sound attenuating element 52 and which further includes a curvilinear handle 254 extending therefrom. The handle 254 includes curved sections such that the handle 254 is offset from and non-collinear with the axis A-A of the sound attenuating element 52. The handle 254 traces a substantially serpentine pattern, i.e., an approximately S-shaped pattern. In a general sense, the stems 202 and 252 include respective handles 204 and 254 which include curvilinear features which result in a non-collinear relationship between the handles and the axis A-A. The stem handles 204, 254 may of course further include additional curved segments and/or linear segments as desired.

Figure 25:
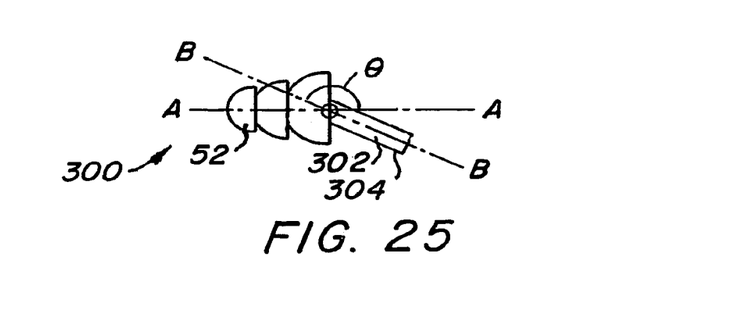

FIG. 25 shows an earplug 300 in another embodiment of the invention. The earplug 300 includes the sound attenuating element 52 and a stem 302 extending therefrom. The stem 302 includes the attachment portion 14 (not shown) and a handle portion 304 extending from the attenuating element 52. The handle portion 304 extends in a substantially linear fashion along the axis B-B which forms the angle Θ with the axis A-A of the sound attenuating element 52. That is, the handle portion 304 is similar to the handle portion 14 of the stem 10 except that, here, the handle 304 does not include a proximate portion collinear with the attenuating element as does the stem 10. To the contrary, the entirety of the handle 304 extends angularly relative to the sound attenuating portion.

The stem handles 204, 254, and 304 of the earplugs 200, 250, and 300, respectively, are shown in the drawings as having a circular cross-section which is of consistent shape and size across a length of the handle. Alternatively, of course, the handles 204, 254, 304 may comprise a variably shaped and/or sized cross-section. The handles 204, 254, 304 can additionally and/or alternatively comprise the handling area 20 and the aperture 22 for receipt and retention of a cord.

The sound attenuating elements 52, 112 discussed herein may be of the push-in type, the roll-down type, or the partial roll-down type. That is, the sound attenuating elements 52, 112, in one embodiment, are inserted into the ear canal by simply placing the element at the entrance of the canal and pushing inwardly on the handle portion 12 of the stem 10, 100. In another embodiment, the sound attenuating element 52, 112 is rolled between the fingers in order to fully compress the element 52, 112 against the attachment portion 14 of the stem 10,100 prior to insertion of the element 52, 112 into the ear canal. In a further embodiment, the attenuating element 52, 112 is compressed only partially prior to insertion.

The various stems 10, 100, 202, 252, 302 described herein may be formed of a plastic or rubber material and may be formed through a molding process, and particularly, by an injection molding process.

As discussed herein in detail, the handle portion 12, 204, 254, 304 of the earplug 50,110,200,250,300 includes a portion which diverges from a longitudinal axis A-A of the respective sound attenuating element 52, 112 by an angle Θ. As mentioned the angle Θ is greater than 90°, preferably between 110° and 140°, and in one exemplary embodiment is less than or equal to about 125°. Thus, at least part of the handle portion 12, 204, 254, 304 of the stem is offset from the respective sound attenuating element 52, 112. When the earplug 50, 110, 200, 250, 300 is inserted into the ear canal of a wearer, some of the angled handle portion 12, 204, 254, 304 remains extending from the ear canal. The angled configuration of the handle portion 12, 204, 254, 304 prevents the stem from excessively protruding from the ear. That is, the angled configuration of the handle portion 12, 204, 254, 304 results in the respective stem lying naturally in the creases or spaces formed in the pinna of the external ear. Preferably, the handle portion 12, 204, 254, 304 of the inserted earplug lies in the intertragic notch of the ear formed below the tragus. As will now be discussed, the angled nature of the handle portion 12,204,254,304 allows the stem of the earplug to extend from the ear canal in an inconspicuous manner, essentially coplanar with respect to a general plane of the outer ear, thus minimizing outer exposure of the stem and hence reducing the likelihood of inadvertent contact.

Figure 26:
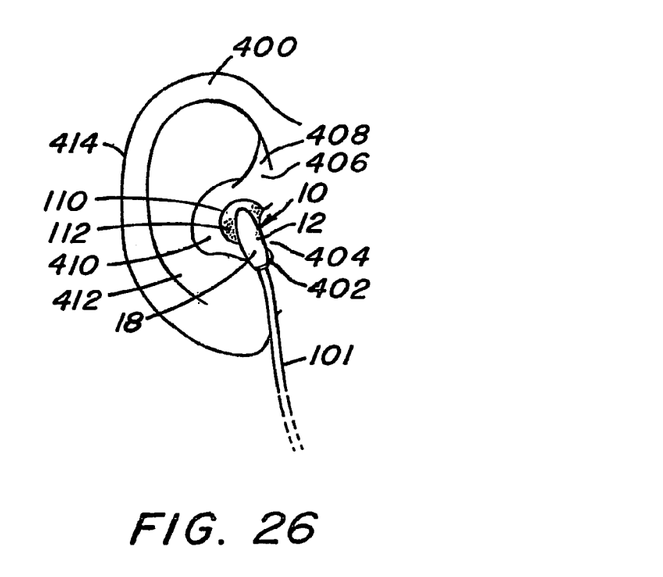
FIG. 26 is a side view of the earplug of FIGS. 16-20 as worn in an ear.
Figure 27:
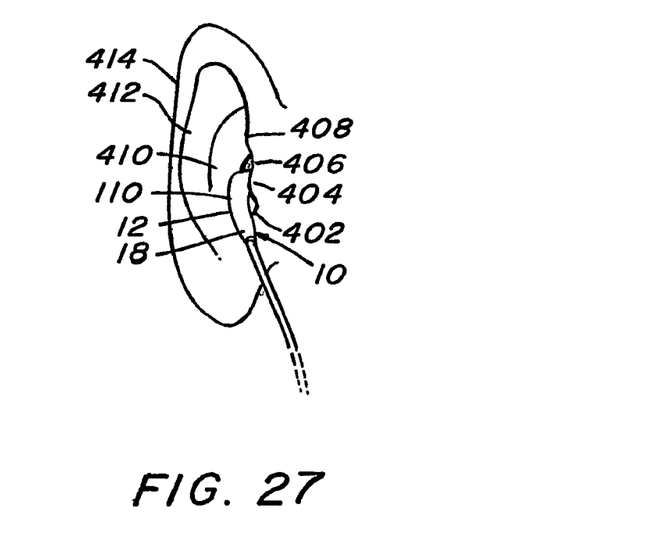
FIG. 27 is a front thereof.
Figure 28:
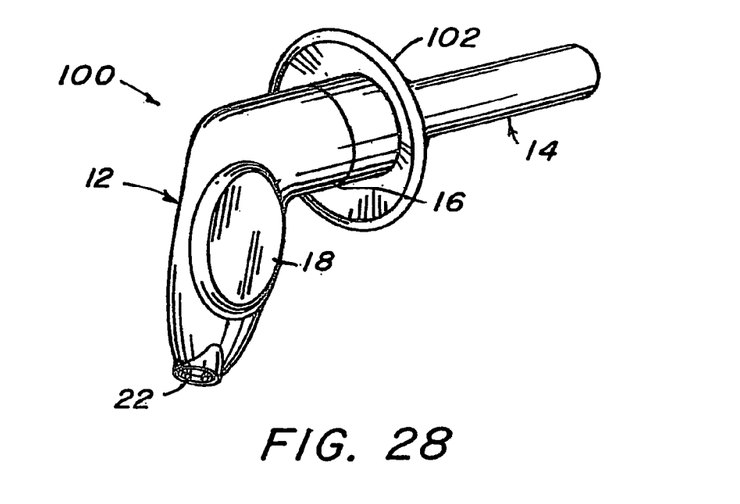
FIG. 28 is a rear perspective view of the stem of FIGS. 11-15.

FIGS. 26-27 show the earplug 110 inserted into an ear canal of a wearer. The sound attenuating portion 112 is lodged within the canal while the handle portion 12 of the stem 10 extends therefrom. The distal portion 18 of the handle portion 12 is angled and configured as discussed above such that, when the earplug 50 is inserted, the portion 18 lies generally in the creases and spaces of the pinna 400 of the external ear. As mentioned, the distal portion 18 preferably lies in the intertragic notch 402 immediately below the tragus 404, as is shown in the drawings. Alternatively, of course, the distal portion 18 may lie in a space 406 above the tragus 404 over the concha 408. Further in the alternative, the portion 18 can extend toward and/or over the anti-tragus 410, anti-helix 412, and helix 414 portions of the external ear. In any event, the portion 18 of the stem 10 which extends from the ear canal of the wearer assumes a low profile by angling over portions of the outer ear rather than projecting straight outward, as is common with conventional earplugs. In this way, the stem 10 is less exposed to body parts of the wearer and of others and out of the way of machinery, structures, clothing, headwear, safety gear, etc. Thus, the stem 10 is configured to avoid some incidental, inadvertent contact and to provide a tighter, less conspicuous profile of the earplug relative to the ear and head of the wearer.

The earplug 50 is shown in FIGS. 26-27 by way of example only. All of the various earplugs discussed herein and additional embodiments contemplated by the invention are configured to be inserted into an ear canal in the same way as and perform similarly to the earplug 50. For example, when the earplug 110 is inserted into an ear canal, the distal portion 18 of the stem 100 extends in an angled manner from the ear canal so as to naturally lie in the creases and spaces of the pinna of the ear such that the stem 100 assumes a low profile relative to the external features of the ear. Similarly, when the earplug 300 is inserted in an ear canal, the handle portion 304 of the stem 302 extends from the canal at an angle and lies in one of the above-designated areas relative to the pinna, thus avoiding an undesired protruding, contactable disposition. In much the same way, when the earplugs 200 and 250 are inserted into an ear canal, the curved nature of the handle portions 204, 254 result in the stems 202, 252 extending from the canal inconspicuously into the creases and folds of the pinna 400.

As shown in FIGS. 26 and 27, the offset nature of the earplug stem 12 relative to the attenuating (inserted) portion 112 directs the cord 101 downward from the ear toward the mandible (not shown) of the wearer. This creates a tight profile of the cord 101 relative to the head of the wearer, thus helping to reduce incidental contact of or with the cord 101. That is, in the illustrated configuration, the cord 101 extends from the stem 10 proximate to the intertragic notch 402 and then directly downward to drape beneath the chin or behind the neck of the wearer, without projecting outward like traditional corded earplugs.

As mentioned above, the earplugs 200, 250, and 300 may include cords attached at ends of the respective stems. In such an embodiment, the curved/angled nature of the stems will direct the cord downward against the ear and mandible of the wearer, as described above with exemplary reference made to FIGS. 26 and 27.

Accordingly, the invention results in a hearing protection device which is inserted, or at least partially inserted, into the ear canal of the wearer and which includes a stem configured so as to extend from the ear canal in an angled or curved manner in or proximate to the natural creases and spaces of the outer ear such that the earplug remains close to the outer ear and, where applicable, directs the cord in a downward manner adjacent the ear, head, and neck of the wearer.

Dimensions and materials identified in this description and the attached Figures are for illustration purposes only and may vary depending upon the intended application in accordance with the teachings of the present invention. The present invention is not intended to be limited to the specific features of the Figures even though the invention encompasses the same.

Furthermore, it will be apparent to those skilled in the art that, while exemplary embodiments have been shown and described, various modifications and variations can be made to the present apparatus and method disclosed herein without departing from the spirit or scope of the invention. Accordingly, it is to be understood that the various embodiments have been described by way of illustration and not limitation.

What is claimed is:

1. A hearing protector, comprising:
   a sound attenuating element; and
   a stem comprising:

a proximal end and a proximal portion adjacent the proximal end, the proximal portion extending along a first longitudinal axis into the sound attenuating element;

a distal end and a distal portion adjacent the distal end, the distal portion extending along a second longitudinal axis and forming a handle, wherein the second longitudinal axis and the first longitudinal axis are not parallel to one another, and the proximal portion and the distal portion connect to form an angle disposed outside of the sound attenuating element; and an aperture at the distal end of the stem to facilitate a cord.

2. The hearing protector of claim 1, wherein the distal portion is connected to the proximal portion by a curved segment.

3. The hearing protector of claim 1, wherein the handle traces a serpentine pattern.

4. The hearing protector of claim 1, wherein the handle comprises a grip feature comprising score lines, protuberances, or both.

5. The hearing protector of claim 1, wherein the aperture is constructed to retain a cord by friction fit or an adhesive agent.

6. The hearing protector of claim 1, further comprising a cord attached to the aperture.

7. The hearing protector of claim 1, wherein the sound attenuating element is attached to the stem by a bonding agent.

8. The hearing protector of claim 1, wherein the sound attenuating element is releasably attached to the stem.

9. The hearing protector of claim 1, wherein the stem comprises a protrusion in the proximal portion protruding transverse to the first longitudinal axis.

10. The hearing protector of claim 9, wherein the sound attenuating element comprises a cavity, and wherein the protrusion is disposed in locking engagement within the cavity to releasably attach the stem to the sound attenuating element.

11. The hearing protector of claim 1, wherein at least a portion of the proximal portion has a proximally decreasing cross-sectional diameter.

12. The hearing protector of claim 1, wherein an entirety of the handle portion extends along the second longitudinal axis.

13. The hearing protector of claim 1, wherein the stem is injection molded plastic.

14. The hearing protector of claim 1, wherein the angle is about 90° to about 140°.

15. The hearing protector of claim 14, wherein the angle is about 125° or less.

16. The hearing protector of claim 1, wherein the sound attenuating element is molded onto the proximal portion of the stem.

17. The hearing protector of claim 1, wherein when the sound attenuating element is inserted into an ear canal of a user, the handle lies adjacent or within the outer ear of the user.

18. The hearing protector of claim 1, wherein the handle is constructed for pushing the sound attenuating element into the ear canal of a user.

19. A hearing protection system comprising:

a first hearing protector and a second hearing protector, each hearing protector comprising:

a sound attenuating element; and a stem extending from a proximal end to a distal end and comprising a proximal portion adjacent the proximal end extending along a first longitudinal axis into the sound attenuating element, and a distal portion adjacent the distal end extending along a second longitudinal axis and forming a handle, wherein the second longitudinal axis and the first longitudinal axis are not parallel to one another, and the proximal portion and the distal portion connect to form an angle disposed outside of the sound attenuating element; and a cord connecting the first and second hearing protectors and coupled with an aperture at the distal end of each of the first and second hearing protectors.

* * * * *

UNITED STATES PATENT AND TRADEMARK OFFICE
CERTIFICATE OF CORRECTION

PATENT NO.       : 10,034,798 B2
APPLICATION NO.  : 13/795790
DATED            : July 31, 2018
INVENTOR(S)      : Robert Falco Page 1 of 1

It is certified that error appears in the above-identified patent and that said Letters Patent is hereby corrected as shown below:

In the Specification

Column 1
Line 25, delete "party" and insert -- partly --, therefor.

Column 2
Line 50, delete "is a is a" and insert -- is a --, therefor.
Line 56, delete "view" and insert -- view of --, therefor.

Column 3
Line 9 (approx.), delete "PREFERED" and insert -- PREFERRED --, therefor.

Signed and Sealed this
Thirteenth Day of November, 2018

Andrei Iancu
*Director of the United States Patent and Trademark Office*